United States Patent [19]

Terao et al.

[11] Patent Number: 4,612,321
[45] Date of Patent: Sep. 16, 1986

[54] 5-PYRIDYL-1,3-THIAZOLE DERIVATIVES

[75] Inventors: Shinji Terao, Osaka; Yoshitaka Maki, Kyoto, both of Japan

[73] Assignee: Takeda Chemical Industries, Inc., Osaka, Japan

[21] Appl. No.: 647,436

[22] Filed: Sep. 5, 1984

[30] Foreign Application Priority Data

Sep. 9, 1983 [JP] Japan .................................. 58-167042
Apr. 17, 1984 [JP] Japan .................................. 59-77819

[51] Int. Cl.⁴ .................... C07D 405/14; A61K 31/44
[52] U.S. Cl. ........................................ 514/338; 514/318; 514/342; 546/280; 546/256; 546/194; 546/270; 544/124; 544/360
[58] Field of Search ............... 546/280, 256, 194, 270; 514/318, 338, 342

[56] References Cited

U.S. PATENT DOCUMENTS 3,705,153 12/1972 Kaneko et al. ................... 546/280
3,963,735 6/1976 Farkas et al. ................... 546/280
4,197,306 4/1980 Harrison et al. ................. 546/280

OTHER PUBLICATIONS

Pendalwas et al., CA 97: 55722v, 1982.
Le Count et al., CA 87: 135172z, 1977.
Jpn Kokai Tokkyo Koho, CA 90: 181605c, 1979.
Reaction of 5-Chloropyridin-2-yl-thioureas with Phenacyl Bromides a New Thiazole Synthesis, J.C.S. Chem. Comm pp. 2282-2833, 1977, David J. Le Count.
N-(4-Substituted-thiazolyl)oxamic Acid Derivatives, a New Series of Potent, Orally Active Antiallergy Agents J. Med Chem. pp. 1158-1163, 1983 Hargrave et al.

*Primary Examiner*—Jane T. Fan
*Attorney, Agent, or Firm*—Wegner & Bretschneider

[57] ABSTRACT

Novel compounds of the formula:

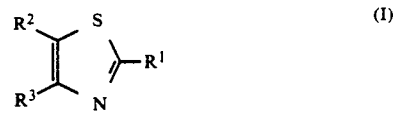

wherein $R^1$ stands for an optionally substituted alkyl group, alkenyl group, aryl group, aralkyl group, cycloalkyl group, heterocyclic group having carbon as the bonding hand or amino group, $R^2$ stands for a pyridyl group which may be substituted with alkyl group, and $R^3$ stands for an optionally substituted aryl group or salts thereof, have analgesic, anti-piretic, anti-inflammatory and anti-ulcer actions, and can be administered to mammals for the therapy of pain, inflammatory diseases, rheumatic chronic diseases.

7 Claims, No Drawings

5-PYRIDYL-1,3-THIAZOLE DERIVATIVES

This invention relates to novel 5-pyridyl-1,3-thiazole derivatives having, among others, analgesic, anti-pyretic, anti-inflammatory, anti-ulcer, thromboxane $A_2(TXA_2)$ synthetase inhibiting, or platelet aggregation inhibiting actions, to a method of preparing same and to pharmaceutical compositions containing same.

Substantially no derivatives of 5-pyridyl-1,3-thiazole have been known. The present inventors synthesized a variety of novel 5-pyridyl-1,3-thiazole derivatives, and subjected them to biological tests to find that those compounds had pharmacological actions such as analgesic, anti-pyretic, anti-inflammatory, anti-ulcer, thromboxane $A_2(TXA_2)$ synthetase inhibitory or platelet aggregation inhibiting actions.

Namely, this invention relates to:

(1) 1,3-thiazole derivatives representable by the general formula:

 (I)

wherein $R^1$ stands for an optionally substituted alkyl group, alkenyl group, aryl group, aralkyl group, cycloalkyl group, heterocyclic group having carbon as the bonding hand or amino group, $R^2$ stands for a pyridyl group which may be substituted with alkyl group, and $R^3$ stands for an optionally substituted aryl group, or salts thereof, (2) a method of preparing a compound representable by the general formula (I) or a salt thereof, characterized by allowing a compound representable by the general formula;

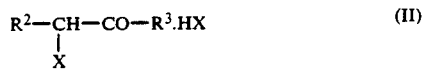 (II)

wherein $R^2$ and $R^3$ have the meanings given above and X stands for a halogen atom to react with a compound representable by the general formula;

 (III)

wherein $R^1$ has the meaning given above, and (3) an analgesic, anti-pyretic, anti-inflammatory and anti-ulcer pharmaceutical composition, which comprises as an active ingredient, an effective amount of a compound representable by the formula (I) or a salt thereof, and a pharmaceutically acceptable carrier therefor.

In the above-mentioned general formulas (I) and (III), alkyl groups represented by $R^1$ may be mentioned those having 1-10 carbon atoms such as methyl, ethyl, n-propyl, i-propyl, n-butyl, i-butyl, n-pentyl, n-hexyl, n-octyl, n-nonyl or n-decyl; alkenyl groups represented by $R^1$ may be mentioned those having 2-4 carbon atoms such as vinyl, allyl, 2-butenyl or isopropenyl; aryl groups represented by $R^1$ may be mentioned phenyl or naphthyl; aralkyl groups represented by $R^1$ may be mentioned phenylalloyl having 7-12 carbon atoms such as benzyl or phenethyl; cycloalkyl groups represented by $R^1$ may be mentioned those having 3-7 carbon atoms such as cyclopropyl, cyclobutyl, cyclopentyl or cyclohexyl; and heterocyclic groups having carbon as the bonding hand representable by $R^1$ are ones containing in its ring one or two hetero atoms such as sulfur, oxygen or nitrogen and may be exemplified thienyl, furyl or thiazole. The alkyl groups, alkenyl groups, aryl groups, aralkyl groups, cycloalkyl groups, heterocyclic groups having carbon as the bonding hand and amino group, which are represented by $R_1$, are all optionally substituted. Substituents of the alkyl groups are exemplified by hydroxyl, amino, a lower alkylamino (those having 1-4 carbon atoms, e.g. methylamino, ethylamino or propylamino), carboxyl, a lower alkoxycarbonyl (those having 2-5 carbon atoms, e.g. methoxycarbonyl, ethoxycarbonyl or n-propoxy-carbonyl). Substituents of the alkenyl groups are exemplified by hydroxyl, a lower alkylamino (alkyl-amino having 1 to 4 carbon atoms e.g. methylamino, ethylamino or propylamino) or carbonyl. Substituents of the aryl group are exemplified by carboxyl, halogen (e.g. fluorine, chlorine or bromine), 2-carboxyethenyl, 2-carboxy-1-propenyl, acetoxy, a lower alkyl (those having 1–4 carbon atoms e.g. methyl, ethyl, propyl, i-propyl, n-butyl, i-butyl or t-butyl. Those substituents can take any optional positions of the cyclic structure. Substituents of the aralkyl groups are exemplified by methoxy or halogen (e.g. chlorine or fluorine), and these can take any optional positions of the cyclic structure. Substituents of the cycloalkyl groups are exemplified by those having 1-3 carbon atoms, e.g. methyl, isopropyl or dimethyl, and one to three of them can take any positions of the cyclic structure. Substituents of the heterocyclic groups having carbon as the bonding hand are exemplified by methyl, acetoxy, benzoyl or nicotinoyl. These substituents can take any optional positions of the cyclic structure. The amino group represented by $R^1$ may also be substituted. The substituents of the amino group are exemplified by a lower alkyl (e.g. those having 1-4 carbon atoms, e.g. methyl, ethyl, n-propyl, i-propyl or n-butyl; aralkyl having 7 to 9 carbon atoms (e.g. benzyl or phenethyl), phenyl, pyridyl (e.g. 2-pyridyl, 3-pyridyl, 4-pyridyl, 5-methyl-3-pyridyl, 4-methyl-2-pyridyl, or 2-methyl-3-pyridyl); a lower alkoxycarbonylacetyl having 4 to 7 carbon atoms (e.g. methoxycarbonylacetyl or ethoxycarbonylacetyl); a lower alkyl carbonyl having 2 to 5 carbon atoms (e.g. acetyl, propionyl or butyloyl); carboxy carbonyl or a lower alkoxycarbonylcarbonyl having 3 to 6 carbon atoms (e.g. methoxycarbonylcarbonyl, or ethoxycarbonylcarbonyl); a lower alkoxycarbonyl having 2 to 4 carbon atoms (e.g. methoxycarbonyl or ethoxycarbonyl); or halogeno-alkyloxy-carbonyl having 2 to 5 carbon atoms (e.g. trichloroethoxycarbonyl or pentafluoroethoxycarbonyl), and the number of these substituents may be one or two. When the amino group has two substituents, they may be combined to each other to form a 5- or 6-membered cyclic amino group, and the cyclic amino group is exemplified by piperidino, morpholino, N-acetylpiperazino or pyrrolidino.

In the general formulae (I) and (II), as the pyridyl group representable by $R^2$, any one of 2-pyridyl, 3-pyridyl or 4-pyridyl may be employed though among them 3-pyridyl is the most preferable, and these may have as a substituent at an optional position of the ring an alkyl group (e.g. a one having one to four carbon atoms, i.e.

methyl, ethyl, n-propyl, i-propyl, n-butyl, i-butyl and t-butyl).

In the general formulae (I) and (II) phenyl group representable by $R^3$ may have as the substituent at optional positions of the ring one to three of lower alkoxy, lower alkyl, hydroxyl or halogen. As the lower alkoxy there may be mentioned ones having one to four carbon atoms such as methoxy, ethoxy and n-propoxy. As the lower alkyl there may be mentioned ones having one to four carbon atoms such as methyl, ethyl and n-propyl. As the halogen there may be mentioned fluorine, chlorine, bromine and iodine. $R^3$ as aryl may be phenyl or naphthyl which at optional adjacent position on the ring may have methylenedioxy, 1,2-ethylenedioxy, trimethylene or tetramethylene group as the substituent.

Compounds representable by the general formula (I) may be addition salts of a pharmacologically acceptable organic acid or inorganic acid. As the acid addition salts there may be mentioned for example ones with hydrochloric acid, hydrobromic acid, phosphoric acid, oxalic acid and methanesulfonic acid.

A compound representable by the general formula (I) can be produced by allowing a compound representable by the general formula (II) with a compound representable by the general formula (III) in the presence of a basic substance. This reaction is usually conducted in a solvent e.g. water, alcohol, acetonitrile, tetrahydrofuran, dimethylformamide and 1,2-dimethoxyethane. The molar ratio of a compound (II) to a compound (III) to be brought into contact with each other is preferably 1:1-1.2. As the basic substance, there may be mentioned for example triethylamine, sodium hydroxide, sodium carbonate and potassium carbonate. The molar ratio of a basic substance to be used is usually within the range from 2.0 to 3.0 relative to the compound (II), preferably 2.0-2.5. The reaction temperature is usually within the range from 0° C. to the boiling point of the solvent used. In this reaction, as the first stage, a compound (II) reacts with a compound (III) to afford a compound representable by the general formula (IV);

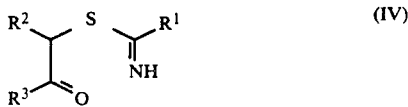

wherein $R^1$, $R^2$ and $R^3$ are of the same meaning as defined above, which undergoes to ring-closure reaction to give a compound (I). In order to conduct these reactions more advantageously, it is preferable to bring a compound (II) into contact with a compound (III) at a temperature not higher than room temperature, then the reaction mixture is heated to a temperature higher than room temperature.

Thus-obtained compound (I) can be isolated and purified by a conventional isolation and purification means such as chromatography, solvent-extraction, crystallization and recrystallization.

The compounds (I) and their salts show excellent antipyretic action, analgesic action, anti-inflammatory action, anti-ulcer action, platelet aggregation controlling action and thromboxane $A_2$ synthesis inhibiting action, and the toxicity thereof is very weak. Thus the compounds (I) can be administered with high safety.

Therefore, the compounds of this invention can be administered to mammals (e.g. human, monkey, cat, dog, horse, cow, mouse, rat etc.) for the therapy of pain, inflammatory diseases, rheumatic chronic diseases, gastroenteric ulcers, ischemic circulation disturbance due to platelet aggregation. They can be orally administered in the form of e.g. tablets, capsules, powder and granule, or non-orally administered in the form of e.g. injection or pellet. The pharmaceutical composition can be prepared by mixing the compound (I) or salt thereof with pharmaceutical acceptable carriers by a conventional manner. The dosage is usually 1 to 10 mg/kg (e.g. 50–500 mg/day/adult) orally and 1 to 20 mg/kg (e.g. 50–200 mg/day/adult) non-orally, and 1–3 times daily.

Among the compounds representable by the general formula (I), 4-[4-phenyl-5-(3-pyridyl)-1,3-thiazole]-butyric acid and 4-[4-(4-methoxyphenyl)-5-(3-pyridyl)-1,3-thiazole]butyric acid have particularly excellent thromboxane synthetase inhibiting action, and 2-phenyl-4-(4-methoxyphenyl)-5-(3-pyridyl)-1,3-thiazole, 2-cyclohexyl-4-(4-methoxyphenyl)-5-(3-pyridyl)-1,3-thiazole and 2-cyclohexyl-4-phenyl-5-(3-pyridyl)-1,3-thiazole have partienlarly excellent platelet aggregation controlling action, and 2-amino-4-(4-methoxyphenyl)-5-(3-pyridyl)-1,3-thiazole, 2-methylamino-4-(4-methoxyphenyl)-5-(3-pyridyl)-1,3-thiazole, 2-ethyl-4-(4-methoxyphenyl)-5-(3-pyridyl)-1,3-thiazole, 2-methylamino-4-(3,4-methylenedioxyphenyl)-5-(3-pyridyl)-1,3-thiazole, 2-methylamino-4-(3,4-trimethylenephenylene)-5-(3-pyridyl)-1,3-thiazole, 2-ethylamino-4-(3,4-methylenedioxyphenyl)-5-(3-pyridyl)-1,3-thiazole, and 2-ethylamino-4-(5-indanyl)-5-(3-pyridyl)-1,3-thiazole have particularly excellent analgesic, anti-pyretic and anti-ulcer actions.

Compounds representable by the general formula (II) can be prepared by, for example, the following process;

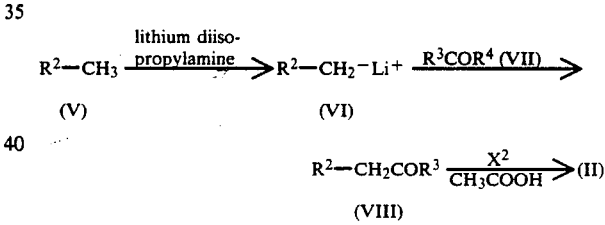

wherein $R^2$, $R^3$ and X are of the same meaning as defined above, and $R^4$ stands for a lower alkoxy group having 1–4 carbon atoms, e.g. methoxy and ethoxy, or dimethylamino, diethylamino, N-phenyl-N-methylamino, N-methoxy-methylamino, pyrrolidino, morphorino and methyl aziridino.

The reaction for leading a compound (V) to a compound (VI) is conducted by allowing the former to react with lithium diisopropylamine. This reaction is usually carried out in a solvent, e.g. anhydrous tetrahydrofuran or anhydrous diethylether at a temperature ranging from −70° C. to 10° C.

The reaction for leading a compound (VI) to a compound (VIII) is conducted by allowing the former to react with a compound (VII). This reaction is usually carried out in a solvent, e.g. as in the above, anhydrous tetrahydrofuran or anhydrous diethylether at a temperature ranging from 0° C. to 20° C.

By allowing a halogen to react with a compound (VIII), a compound (II) can be obtained. This reaction is conducted by allowing a halogen e.g. chlorine or bromine to react with a compound (VIII) in a solvent such as acetic acid. The reaction temperature usually ranges from 10° C. to 100° C. and the reaction time usually ranges from one to ten hours. The reaction product is allowed to precipitate as insoluble salt by addition of ether, isopropylether or the like, then the solvent is removed, followed by crystallization of the residue from ethanol, ethyl acetate, methanol or the like for refining.

Compounds representable by the general formula (III) can be prepared by, for example, the following process;

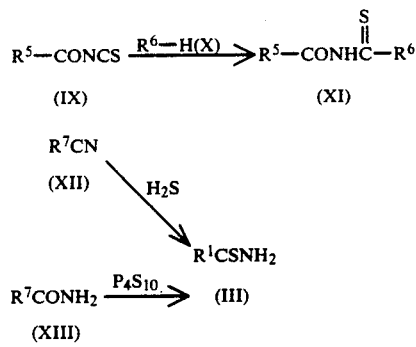

wherein $R^1$ is of the same meaning as defined above, $R^5$ stands for methoxy, ethoxy or phenyl group, $R^6$ stands for a cyclic amino, di-substituted lower alkylamino or diphenylamino group, and $R^7$ stands for substituent shown by $R^1$ except di-substituted amino.

For leading a compound (IX) to a compound (XI), the former is allowed to react with a compound (X). This reaction is conducted in an organic solvent. As the solvent are mentioned, for example, methylene chloride and chloroform. The ratio of a compound (IX) to be brought into contact with a compound (X) is usually 1.0–1.5 mol. relative to 1 mol. of a compound (IX). The reaction temperature usually ranges from 0° C. to 50° C., and the reaction time is usually within the range from one to five hours.

For leading a compound (XI) to a compound (III), a conventional alkaline or acid hydrolysis is usually employed. For the alkaline hydrolysis is used sodium hydroxide or potassium hydroxide, and for the acid hydrolysis is used hydrochloric acid or hydrobromic acid. As a solvent is employed water or an aqueous organic solvent (ethanol, methanol, dioxane, etc.).

For leading a compound (XII) to a compound (XIV), the former compound is allowed to react with hydrogen sulfide under basic conditions. As a base is preferably employed triethylamine or pyridine, and as a reaction solvent is employed, for example, methylene chloride, chloroform, triethylamine or pyridine. The reaction is usually conducted at a temperature ranging from −10° C. to 30° C. under normal pressure or elevated pressure.

For leading a compound (XIII) to a compound (III), the former compound is allowed to react with $P_4S_{10}$. This reaction is conducted in an organic solvent such as ether, tetrahydrofuran, methylene chloride and chloroform at a temperature ranging from room temperature to the boiling point of a solvent employed. The amount of phosphorus pentasulfide (as $P_4S_{10}$) is within the range of from 0.5 mol to 1.2 mol relative to the compound (XIII).

The following working examples, experimental examples and reference examples will explain the present invention more concretely.

EXAMPLE 1

In 18 ml of acetonitrile was dissolved 242 mg of N-methylthiourea. In the solution was suspended 1.0 g of 2-bromo-1-(4-methoxyphenyl)-2-(3-pyridyl)ethanone hydrobromide. To the suspension was added dropwise slowly 0.4 ml of triethylamine while stirring. The mixture was stirred for three hours at refluxing temperature, and the solvent was evaporated off. To the residue was added a saturated aqueous solution of sodium hydrogen carbonate. The mixture was subjected to extraction with ethyl acetate. The extract was dried, then the solvent was evaporated off. The residue was recrystallized from ethyl acetate isopropyl ether to yield 650 mg (85%) of 4-(4-methoxyphenyl)-2-methylamino-5-(3-pyridyl)-1,3-thiazole, m.p. 158°–159° C.

EXAMPLE 2

In 40 ml of acetonitrile was dissolved 516 mg of thiourea. In the solution was suspended 2.5 g of 2-bromo-1-(4-methoxyphenyl)-2-(3-pyridyl)-ethanone hydrobromide. To the suspension was added dropwise slowly 0.95 ml of triethylamine while stirring. The mixture was stirred for 3 hours at a refluxing temperature, which was then left standing for cooling. Precipitating crystals were collected by filtration. The crystals were washed with an aqueous solution of saturated hydrogen carbonate, water, ethanol and ethylether in that order, followed by drying. The crystals were recrystallised from tetrahydrofuran to yield 1.5 g (90%) of 2-amino-4-(4-methoxyphenyl)-5-(3-pyridyl)-1,3-thiazol, m.p. 265°–266° C.

EXAMPLE 3

In 40 ml of acetonitrile was dissolved 493 mg of thiopropionic acid amide. In the solution was suspended 2.15 g of 2-bromo-1-(4-methoxyphenyl)-2-(3-pyridyl)ethanone. To the suspension was added dropwise slowly 0.78 ml of triethylamine while stirring. The mixture was stirred for 3 hours at a refluxing temperature, then the solvent was evaporated off. To the residue was added a saturated aqueous solution of sodium hydrogen carbonate. The mixture was subjected to extraction with ethyl acetate. The extract was dried, then the solvent was evaporated off. The residue was recrystallised from ethyl acetate-isopropyl ether to yield 1.38 g (91%) of 2-ethyl-4-(4-methoxyphenyl)-5-(3-pyridyl)-1,3-thiazole, m.p. 59°–60° C.

EXAMPLE 4

In 40 ml of acetonitrile was suspended 2.26 g of 2-bromo-1-(4-methoxyphenyl)-2-(3-pyridyl)ethanone hydrobromide. To the suspension was added 1.0 g of 4-methoxycarbonyl butane thioamide. To the mixture was added dropwise 0.8 ml of triethylamine while stirring. The mixture was stirred for 3 hours at a refluxing temperature. The solvent was evaporated off. To the residue was added a saturated aqueous solution of sodium hydrogen carbonate. The resultant mixture was subjected to extraction with ethyl acetate, and the extract was washed with water, dried and concentrated. The concentrate was purified by means of a silica-gel column chromatography [ethyl acetate-isopropylether (1:1)] to yield 1.5 g (72.6%) of 2-(3-methoxycarbonylpropyl)-4-(4-methoxyphenyl)-5-pyridyl)-1,3-thiazole as an oily substance.

EXAMPLE 5

In 5 ml of methanol was dissolved 1.5 g of 2-(3-methoxycarbonylpropyl)-4-(4-methoxyphenyl)-5-(3-pyridyl)-1,3-thiazole obtained in Example 4. To the solution was added 1.5 g of sodium hydroxide dissolved in 5 ml of water. The mixture was stirred for 2 hours at 80° C. To the resultant was added water, pH of which was adjusted to 6.0 with 1N-HCl. The aqueous solution was subjected to extraction with ethyl acetate. The organic layer was washed with water, dried and concentrated. The resulting crystals were recrystallised from ethyl acetate to yield 1.2 g (83%) of 2-(3-carboxypropyl)-4-(4-methoyphenyl)-5-(3-pyridyl)-1,3-thiazole, m.p. 163°-164° C.

EXAMPLE 6

In 10 ml of tetrahydrofuran was dissolved 770 mg of 2-(3-methoxycarbonylpropyl)-4-(4-methoxyphenyl)-5-(3-pyridyl)-1,3-thiazole prepared by example 4, which was then cooled with ice. To the solution was added little by little 100 mg of lithium aluminium hydride, which was stirred for one hour. To the mixture was added water, which was subjected to extraction with ethyl acetate. The organic layer was washed with water, dried and concentrated, followed by purifying by means of a silica-gel chromatography [chloroform-methanol (9:1)] to yield 576 mg (81%) of 2-(4-hydroxybutyl)-4-(4-methoxyphenyl)-5-(3-pyridyl)-1,3-thiazole as an oily substance.

EXAMPLE 7

In 5 ml of dimethylformamide was dissolved 1 g of 2-amino-4-(4-methoxyphenyl)-5-(3-pyridyl)-1,3-thiazole. To the solution was added under ice-cooling 580 mg of ethoxycarbonylacetylchloride. The mixture was stirred for 30 minutes, to which was then added a saturated aqueous solution of sodium hydrogen chloride. The resultant was subjected to extraction with ethyl acetate. The organic layer was washed with water, dried and concentrated, followed by recrystallization from tetrahydrofuran to give 850 mg (61%) of 2-ethoxycarbonylacetylamino-4-(4-methoxyphenyl)-5-(3-pyridyl)-1,3-thiazole, m.p. 202°-203° C.

EXAMPLE 8

To 15 ml of acetonitrile were added 1.0 g of 2-bromo-1-(4-methoxyphenyl)-2-(3-pyridyl)ethanone hydrobromide and 387 mg 1-piperazine carbothioamide. To the mixture was slowly added 0.4 ml of triethylamine while stirring. The whole mixture was stirred for 2 hours at refluxing temperature, then the solvent was evaporated off. To the residue was added a saturated aqueous solution of sodium hydrogen carbonate, which was subjected to extraction with ethyl acetate. The extract was dried and the solvent was evaporated off. The residue was dissolved in 2 ml of pyridine, and the solution was cooled with ice, to which was added 0.3 ml of acetylchloride. The mixture was left standing at room temperature for one hour. The reaction solution was poured into ice-water, followed by extraction with ethyl acetate. The extract solution was washed with water, dried and concentrated. The concentrate was purified by means of a silica-gel column chromatography [ethyl acetate-methanol (9:1)] to yield 300 mg (28%) of 2-(4-acetyl-1-piperazinyl)-4-(4-methoxyphenyl)-5-(3-pyridyl)-1,3-thiazole.

EXAMPLE 9

In 3.2 ml of 1% MeOH-HCl was dissolved 2-amino-4-(4-methoxyphenyl)-5-(3-pyridyl)-1,3-thiazole. The solvent was evaporated off. The residue was recrystallized from methanol-ethyl acetate to yield 180 mg (80%) of 2-amino-4-(4-methoxyphenyl)-5-(3-pyridyl)-1,3-thiazole hydrochloride, m.p. 145°-150° C.

EXAMPLE 10

In 40 ml of acetonitrile was dissolved 661 mg. of N-methyl thiourea. In the solution was suspended 2.9 g of 2-bromo-1-(5-indanyl)-2-(3-pyridyl)ethanone hydrobromide. To the suspension was added dropwise slowly 1 ml of triethylamine. The mixture was then stirred for 2 hours at refluxing temperature, followed by being left standing for cooling. The solvent was then evaporated off. To the residue was added a saturated aqueous solution of sodium hydrogen carbonate. The mixture was subjected to extraction with ethyl acetate. The extract solution was washed with water, dried and, then, the solvent was evaporated off. Recrystallization was conducted from ethyl acetate-isopropylether afforded 1.8 g (80%) of 4-(5-indanyl)-2-methylamino-5-(3-pyridyl)-1,3-thiazole, m.p. 169°-170° C.

EXAMPLE 11

In 40 ml of acetonitrile was dissolved 1.12 g of benzyloxycarbonylaminothioacetamide. In the solution was suspended 2.0 g of 2-bromo-1-(4-methoxyphenyl)-2-(3-pyridyl)ethanone hydrobromide. To the suspension was added while stirring 0.8 ml of triethylamine. The mixture was stirred for 2 hours under reflux. The resultant was left standing for cooling, then the solvent was evaporated off. To the residue was added a saturated aqueous solution of sodium hydrogen carbonate. The mixture was subjected to extraction with ethyl acetate. The extract solution was washed with water, dried and, then, the solvent was evaporated off. The residue was recrystallized from ethyl acetate-isopropylether to give 1.3 g (yield 56%) of 2-(benzyloxycarbonylaminomethyl)-4-(4-methoxyphenyl)-5-(3-pyridyl)-1,3-thiazole, m.p. 93°-94° C.

EXAMPLE 12

In 10 ml of tetrahydrofuran was dissolved 1.2 g of 2-(benzyloxycarbonylaminomethyl)-4-(4-methoxyphenyl)-5-(3-pyridyl)-1,3-thiazole obtained by Example 11. To the solution was added 10 ml of 5N-HCl, and the mixture was stirred for 2 hours at 80° C. Tetrahydrofuran was evaporated off under reduced pressure. The remaining aqueous layer was made alkaline with 2N-NaOH, which was subjected to extraction with ethyl acetate. The extract was washed with water and dried, then the solvent was evaporated off. The residue was purified by means of a silica-gel column chromatography [eluent: chloroform-methanol (9:1)] to give 0.5 g (yield 60%) of 2-(aminomethyl)-4-(4-methoxyphenyl)-5-(3-pyridyl)-1,3-thiazole.

EXAMPLE 13

In 50 ml of acetonitrile was dissolved 2.3 g of N-methylbenzoylaminothioacetamide. In the solution was suspended 4.0 g of 2-bromo-1-(4-methoxyphenyl)-2-(3-pyridyl)ethanone hydrobromide. To the suspension was added while stirring 1.5 ml of triethylamine, followed by further stirring under reflux. The reaction solution was left standing for cooling, then the solvent was evaporated off. To the residue was added a saturated aqueous solution of sodium hydrogen carbonate. The mixture was subjected to extraction with ethyl acetate. The extract solution was washed with water, dried, then, the solvent was evaporated off. The residue was purified by means of a silica-gel column chromatography (eluent: ethyl acetate) to give 3.2 g (yield 72%) of 2-(N-methyl-benzoylaminomethyl)-4-(4-methoxyphenyl)-5-(3-pyridyl)-1,3-thiazole.

EXAMPLE 14

To 2-(N-methyl(benzoylaminomethyl)-4-(4-methoxyphenyl)-5-(3-pyridyl)-1,3-thiazole obtained by Example 13 was added 20 ml of 5N-HCl, and the mixture was stirred for 2 hours at 80° C. The reaction solution was left standing for cooling, which was then made alkaline with 2N-NaOH. The alkaline solution was subjected to extraction with ethyl acetate. The extract solution was washed with water, dried and concentrated under reduced pressure, followed by purification by means of a silica-gel column chromatography [eluent: chloroform-methanol (9:1)] to give 2.1 g (yield 91%) of 4-(4-methoxyphenyl)-2-methylaminomethyl-5-(3-pyridyl)-1,3-thiazole. Compounds prepared after the manner described in the above Examples 1–9 are exemplified in Table 1. Melting points are all uncorrected.

TABLE 1

| Cmpd No. | No. of W. Ex. based | $R^1$ | $R^2$ | $R^3$ | Composition Formula | m.p. |
|---|---|---|---|---|---|---|
| 1 | 1 | —NHMe | 3-pyridyl | 4-MeO-phenyl | $C_{16}H_{15}N_3OS$ | 158–159° |
| 2 | 2 | —NH$_2$ | 3-pyridyl | 4-MeO-phenyl | $C_{15}H_{13}N_3OS$ | 265–266° |
| 3 | 1 | —NHMe | 3-pyridyl | phenyl | $C_{15}H_{13}N_3S$ | 168–169° |
| 4 | 2 | —NH$_2$ | 3-pyridyl | phenyl | $C_{14}H_{11}N_3S$ | 253–254° |
| 5 | 2 | —NH$_2$ | 3-pyridyl | 3,4-diMeO-phenyl | $C_{16}H_{15}N_3O_2S$ | 240–241° |
| 6 | 2 | —NH$_2$ | 3-pyridyl | 3,4,5-triMeO-phenyl | $C_{17}H_{17}N_3O_3S$ | 168–169° |
| 7 | 1 | —NHMe | 3-pyridyl | 4-F-phenyl | $C_{15}H_{12}N_3FS$ | 157–158° |
| 8 | 1 | —NHMe | 6-Me-3-pyridyl | phenyl | $C_{16}H_{15}N_3S$ | 205–206° |

|  |  |  |  |  |  |
|---|---|---|---|---|---|
| 9 | 2 | —NH₂ | 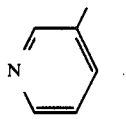 | 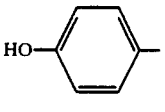 | $C_{14}H_{11}N_3OS$ 266–268° |
| 10 | 7 | —NHCOMe | 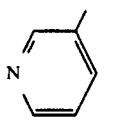 | 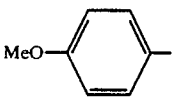 | $C_{17}H_{15}N_3O_2S$ 119–120° |
| 11 | 7 | —NHCOCH₂CO₂Et | 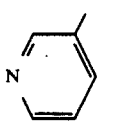 | 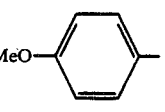 | $C_{20}H_{19}N_3O_4S$ 201–202° |
| 12 | 7 | —NHCOCH₂CO₂Me | 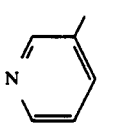 | 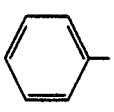 | $C_{18}H_{15}N_3O_3S$ 185–186° |
| 13 | 2 | —NH₂ | 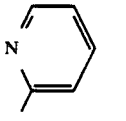 | 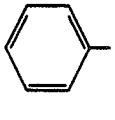 | $C_{14}H_{11}N_3S$ 236–237° |
| 14 | 1 | —NHMe | 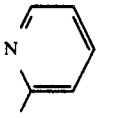 | 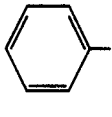 | $C_{15}H_{13}N_3S$ 215–216° |
| 15 | 1 | —NHMe | 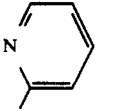 | 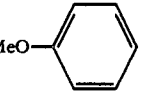 | $C_{16}H_{15}N_3OS$ 214–215° |
| 16 | 2 | —NH₂ | 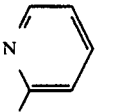 | 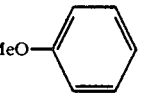 | $C_{15}H_{13}N_3OS$ 217–218° |
| 17 | 2 | —NH₂ | 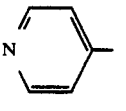 | 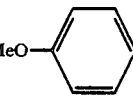 | $C_{15}H_{13}N_3OS$ 282–284° |
| 18 | 2 | —NH₂ | 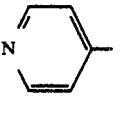 | 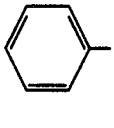 | $C_{14}H_{11}N_3S$ 248–250° |
| 19 | 1 | —NHMe | 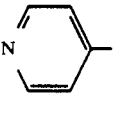 | 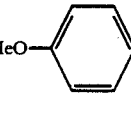 | $C_{16}H_{15}N_3OS$ 177–178° |
| 20 | 1 | 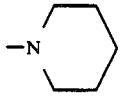 | 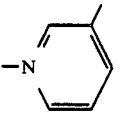 | 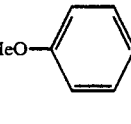 | $C_{20}H_{21}N_3OS$ 130–131° |

TABLE 1-continued
| | | | | | |
|---|---|---|---|---|---|
| 21 | 1 | 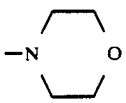 | 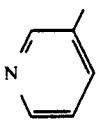 | 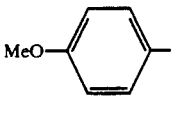 | $C_{19}H_{19}N_3O_2S$ 134–135° |
| 22 | 3 | —CH$_2$CH$_3$ | 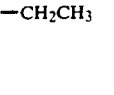 | 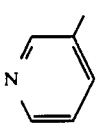 | $C_{19}H_{20}N_2O_3S$ 84–84.5° |
| 23 | 3 | —CH$_2$CH$_3$ | 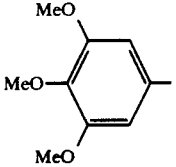 | 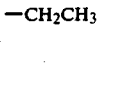 | $C_{17}H_{16}N_2OS$ 59–60° |
| 24 | 3 | —CH$_2$CH$_3$ | 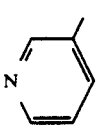 | 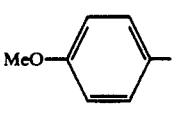 | $C_{16}H_{14}N_2OS$ 174–175° |
| 25 | 3 | —CH$_3$ | 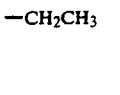 | 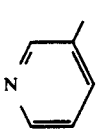 | $C_{16}H_{14}N_2OS$ 113–114° |
| 26 | 3 | —CH$_2$CH$_3$ | 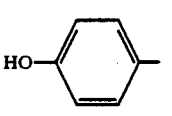 | 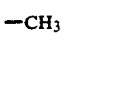 | $C_{16}H_{14}N_2S$ |
| 27 | 3 | 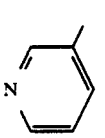 | 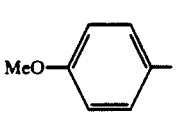 | 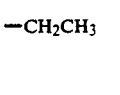 | $C_{20}H_{14}N_2S$ 135–136° |
| 28 | 3 | 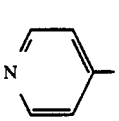 | 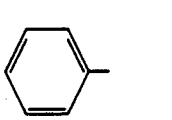 | 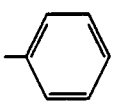 | $C_{21}H_{16}N_2OS$ 104–105° |
| 29 | 3 |  | 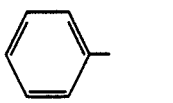 | 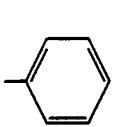 | $C_{22}H_{18}N_2O_2S$ 96–98° |
| 30 | 1 |  | 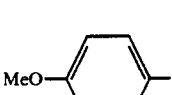 |  | $C_{21}H_{17}N_3OS$ 195–196° |
| 31 | 1 |  |  | 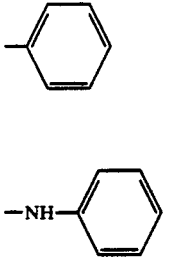 | $C_{23}H_{21}N_3O_3S$ 211–213° |

TABLE 1-continued

| # | | R1 | R2 | R3 | Formula | mp |
|---|---|---|---|---|---|---|
| 32 | 1 | -NH-C6H5 | 3-methylpyridyl | 4-HO-C6H4- | C20H15N3OS | 280–282° |
| 33 | 3 | cyclohexyl | 3-methylpyridyl | C6H5- | C20H20N2S | 100–101° |
| 34 | 3 | cyclohexyl | 3-methylpyridyl | 4-MeO-C6H4- | C21H22N2OS | 92–93° |
| 35 | 3 | cyclohexyl | 3-methylpyridyl | 3,4,5-(MeO)3-C6H2- | C23H26N2O3S | 111–112° |
| 36 | 4,5 | 4-HOOC-C6H4- | 3-methylpyridyl | 4-MeO-C6H4- | C22H16N2O3S | 264–265° |
| 37 | 4,5 | 4-HOOC-C6H4- | 3-methylpyridyl | 3,4-(MeO)2-C6H3- | C23H18N2O4S | 245–246° |
| 38 | 4,5 | 4-HOOC-C6H4- | 3-methylpyridyl | 3,4,5-(MeO)3-C6H2- | C24H20O5N2S | 247–248° |
| 39 | 3 | —Me | 3-methylpyridyl | 4-(HOOCCH=CH)-C6H4- | C18H14N2O2S | 208–109° |
| 40 | 4,5 | 4-(HOOCCH=CH)-C6H4- | 3-methylpyridyl | C6H5- | C23H16O2N2S | 255–256° |
| 41 | 4,5 | 4-(HOOC-C(Me)=CH)-C6H4- | 3-methylpyridyl | 3,4-(MeO)2-C6H3- | C26H22O4N2S | 225–226° |
| 42 | 4,5 | —(CH2)3COOH | 3-methylpyridyl | C6H5- | C18H16N2O2S | 143–144° |

TABLE 1-continued
| 43 | 4,5 | —(CH₂)₃COOH | 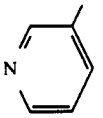 | 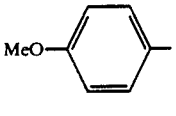 | C₁₉H₁₈N₂O₃S 163–164° |
| 44 | 4,5 | —(CH₂)₃COOH | 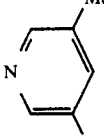 | 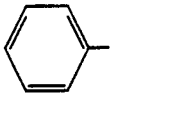 | C₁₉H₁₈N₂O₂S 134–135° |
| 45 | 4,5 | —(CH₂)₈COOH | 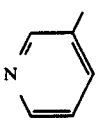 | 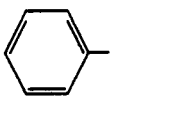 | C₂₃H₂₆ 112–113° |
| 46 | 4,6 | —(CH₂)₄OH | 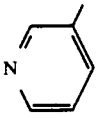 | 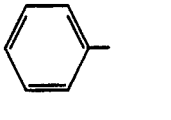 | C₁₈H₁₈N₂OS 51–52° |
| 47 | 1 | —NHCH₂CH₃ | 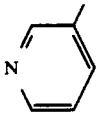 | 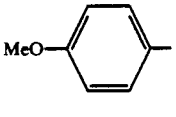 | C₁₇H₁₇N₃OS 154–155° |
| 48 | 1 | —NHMe |  | 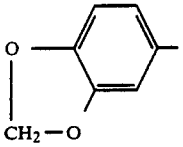 | C₁₆H₁₃N₃O₂S 187–188° |
| 49 | 1 | —NHMe | 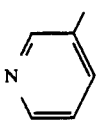 | 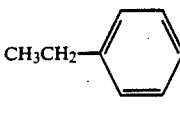 | C₁₇H₁₇N₃S 124–125° |
| 50 | 9 | —NH₂ | 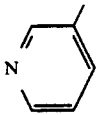 | 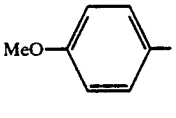 | C₁₅H₁₃N₃OS.HCl 145–150° |
| 51 | 1 | —NHMe | 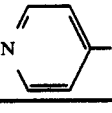 | 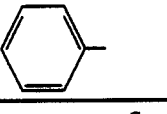 | C₁₅H₁₃N₃S 191–192° |
| Cmpd No. | No. of W. Ex. based | R¹ | R² | R³ | Composition Formula | NMR, δ$_{ppm}$(CDCl₃) |
|---|---|---|---|---|---|---|
| 52 | 1 | —N(C₂H₅)₂ | 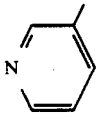 | 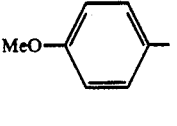 | C₁₉H₂₁N₃OS | 1.27(6H),3.52(4H),3.77(3H),6.78(2H),7.07(1H),7.40(2H),7.50(1H),8.37(1H),8.50(1H) |
| 53 | 8 | 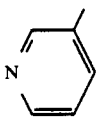 | 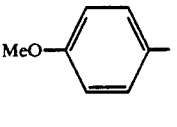 |  | C₂₁H₂₂N₄O₂S | 2.13(3H),3.60(6H),3.77(5H),6.78(2H),7.17(1H),7.38(2H),7.53(1H),8.42(1H),8.52(1H) |

TABLE 1-continued

| | | | | | | |
|---|---|---|---|---|---|---|
| 54 | 1 | —N(Me)₂ | 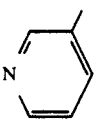 | 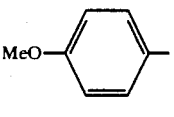 | C₁₇H₁₇N₃OS | 3.12(6H),3.77(3H),6.78(2H),7.07(1H),7.40(2H),7.50(1H),8.37(1H),8.50(1H) |
| 55 | 3 | —CH₂CH₃ | 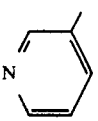 | 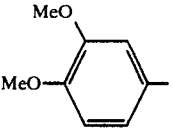 | C₁₈H₁₈N₂O₂S | 1.43(3H),3.07(2H),3.70(3H),3.87(3H),6.75(1H),7.00(2H),7.20(1H),7.60(1H),8.48(1H),8.60(1H) |
| 56 | 3 | —CH₂CH₃ | 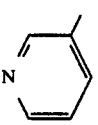 | 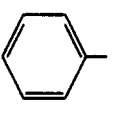 | C₁₆H₁₄N₂S | 1.40(3H),3.05(2H),6.87(1H),7.27(5H),7.57(1H),8.47(1H),8.57(1H) |
| 57 | 3 | —CH₂CH₂CH₂CH₃ | 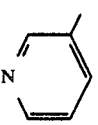 | 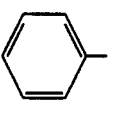 | C₁₈H₁₈N₂S | 0.97(3H),1.48(2H),1.85(2H),3.05(2H),7.23(1H),7.27(5H),7.57(1H),8.50(1H),8.57(1H) |
| 58 | 3 | —CH₂CH₃ | 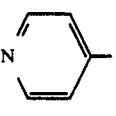 | 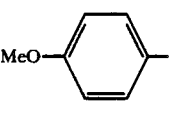 | C₁₇H₁₆N₂OS | 1.43(3H),3.07(2H),3.80(3H),6.83(2H),7.18(2H),7.43(2H),8.50(2H) |
| 59 | 3 | 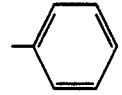 | 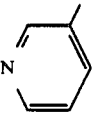 | 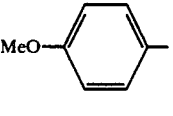 | C₂₂H₂₄N₂O₂S | 3.73(3H),3.87(3H),6.80(1H),7.00~7.80(7H),8.03(2H),8.53(1H),8.67(1H) |
| 60 | 4,5 | —CH₂COOH | 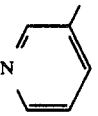 | 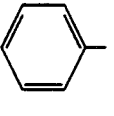 | C₁₆H₁₂N₂O₂S | 2.77(2H),7.20–7.70(7H),8.60(2H),10.40(1H) |
| 61 | 4 | —(CH₂)₃COOMe | 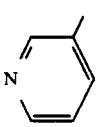 | 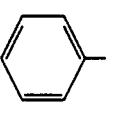 | C₁₉H₁₈N₂O₂S | 2.00(2H),2.17(2H),2.50(2H),3.59(3H),3.67(3H),7.17(1H),7.30(5H),7.82(1H),8.47(1H),8.70(1H) |
| 62 | 4,5 | —(CH₂)₅COOH |  | 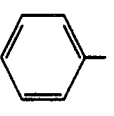 | C₂₀H₂₀N₂O₂S | 1.40–2.10(6H),2.37(2H),3.05(2H),7.10–7.70(7H),8.50(1H),8.57(1H),10.50(1H) |
| 63 | 4,5 | —(CH₂)₅COOH | 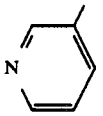 | 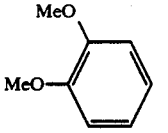 | C₂₂H₂₄N₂O₄S | 1.40–2.10(6H),2.37(2H),3.07(2H),3.70(3H),3.83(3H),6.75(1H),6.97(2H),7.23(1H),7.63(1H),8.50(1H),8.60(1H),10.10(1H) |
| 64 | 4,6 | —(CH₂)₄OH | 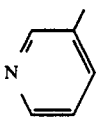 | 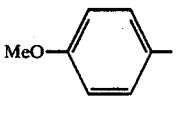 | C₁₉H₂₀N₂O₂S | 1.60–2.20(5H),3.07(2H),3.70(2H),3.77(3H),6.80(2H),7.20(1H),7.37(2H),7.58(1H),8.50(1H),8.57(1H) |
| 65 | 4,6 | —(CH₂)₆OH | 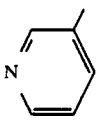 | 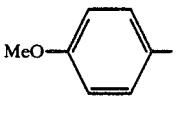 | C₂₁H₂₄N₂O₂S | 1.40–2.00(8H),2.30(1H),3.03(2H),3.60(2H),3.77(3H),6.80(2H),7.26(1H),7.40(2H),7.60(1H),8.47(1H),8.56(1H) |

TABLE 1-continued

| Cmpd No. | No. of W. Ex. based | R¹ | R² | R³ | Composition Formula | m.p. |
|---|---|---|---|---|---|---|
| 66 | 3 | —CH₂CH₂CH₃ | 3-pyridyl | 4-MeO-phenyl | $C_{18}H_{18}N_2OS$ | 1.03(3H),1.87(2H),3.00(2H),3.77(3H),6.78(2H),7.17(1H),7.38(2H),7.57(1H),8.47(1H),8.57(1H) |
| 67 | 3 | —CH(CH₃)₂ | 3-pyridyl | 4-MeO-phenyl | $C_{18}H_{18}N_2OS$ | 1.40(3H),1.50(3H),3.35(1H),3.77(3H),6.78(2H),7.17(1H),7.38(2H),7.58(1H),8.47(1H),8.57(1H) |
| 68 | 1 | N(Me)₂ | 3-pyridyl | 3,4-methylenedioxyphenyl | $C_{17}H_{15}N_3O_2S$ | 76–77° |
| 69 | 1 | N(CH₂CH₃)₂ | 3-pyridyl | 3,4-methylenedioxyphenyl | $C_{19}H_{19}N_3O_2S$ | 97–98° |
| 70 | 1 | NHMe | 4-pyridyl | 3,4-methylenedioxyphenyl | $C_{16}H_{13}N_3O_2S$ | 234–235° |
| 71 | 1 | N(Me)₂ | 4-pyridyl | 3,4-methylenedioxyphenyl | $C_{17}H_{15}N_3O_2S$ | 144–145° |
| 72 | 1 | NHMe | 3-pyridyl | 3-MeO-phenyl | $C_{16}H_{15}N_3OS$ | 146–147° |
| 73 | 1 | NHMe | 3-pyridyl | 2-Me-phenyl | $C_{16}H_{15}N_3OS$ | 153–154° |
| 74 | 1 | NHMe | 4-pyridyl | 4-F-phenyl | $C_{15}H_{12}N_3FS$ | 205–206° |
| 75 | 1 | NHMe | 4-pyridyl | 4-Cl-phenyl | $C_{15}H_{12}N_3ClS$ | 224–225° |
| 76 | 1 | NHMe | 4-pyridyl | 4-Br-phenyl | $C_{15}H_{12}N_3BrS$ | 206–207° |

TABLE 1-continued

| # | | | | | Formula m.p. |
|---|---|---|---|---|---|
| 77 | 1 | NHMe | 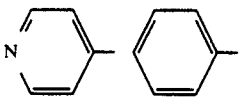 | 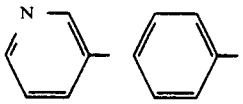 | C₁₅H₁₃N₃S 191–192° |
| 78 | 1 | NHMe | 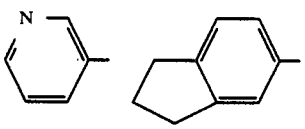 | 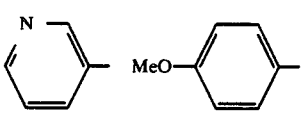 | C₁₅H₁₃N₃S 144–145° |
| 79 | 10 | NHMe | 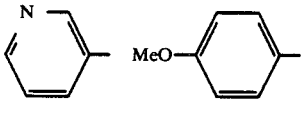 | 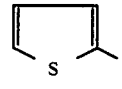 | C₁₈H₁₇N₃S 169–170° |
| 80 | 1 | NHCH₂CH₂—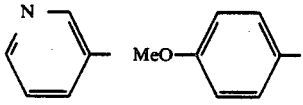 | 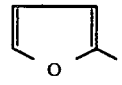 | MeO—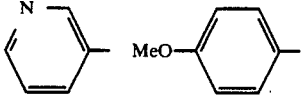 | C₂₃H₂₁N₃OS 126–127° |
| 81 | 1 | 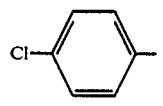 | 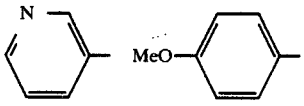 | MeO—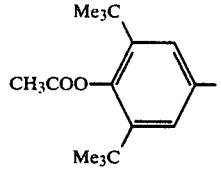 | C₂₀H₁₆N₄OS 222–223° |
| 82 | 3 | 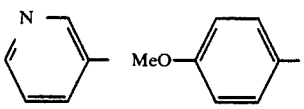 | 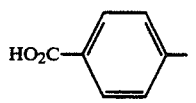 | MeO—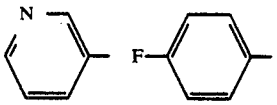 | C₁₉H₁₄N₂OS₂ 132–133° |
| 83 | 3 | 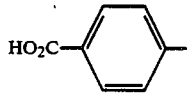 | 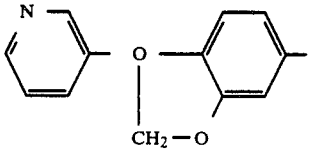 | MeO—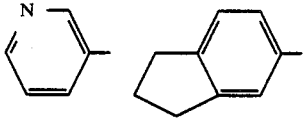 | C₁₉H₁₄N₂O₂S 90–91° |
| 84 | 3 | Cl— (phenyl) | (pyridyl) | MeO— (phenyl) | C₂₁H₁₅N₂OClS 148–149° |
| 85 | 3 | Me₃C / CH₃COO / Me₃C (substituted phenyl) | (pyridyl) | MeO— (phenyl) | C₃₁H₃₄N₂O₃S 180–181° |
| 86 | 4,5 | HO₂C— (phenyl) | (pyridyl) | F— (phenyl) | C₂₁H₁₃N₂O₂SF 240–241° |
| 87 | 4,5 | HO₂C— (phenyl) | (pyridyl) | O—CH₂—O (methylenedioxyphenyl) | C₂₂H₁₄N₂O₄S 258–259° |
| 88 | 10 | N(Me)₂ | (pyridyl) | (indanyl) | C₁₉H₁₉N₃S 85–86° |

TABLE 1-continued

| | | | | | |
|---|---|---|---|---|---|
| 89 | 10 | N(CH₂CH₃)₂ | 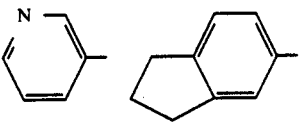 | | C₂₁H₂₃N₃S 56-57° |

| Cmpd No. | No. of W. Ex. based | R¹ | R² | R³ | Composition Formula | NMR $\delta_{ppm}$(CDCl₃) |
|---|---|---|---|---|---|---|
| 90 | 11,12 | CH₂NH₂ | 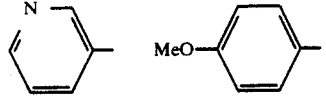 | | C₁₆H₁₅N₃OS | 1.90(2H),3.80(3H),4.20 (2H),6.80(2H),7.27(1H), 7.38(2H),7.62(1H),8.50 (1H),8.60(1H) |
| 91 | 13,14 | CH₂NHMe | 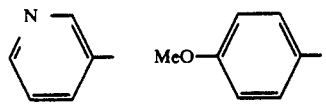 | | C₁₇H₁₇N₃OS | 1.86(1H),2.60(3H),3.78 (3H),4.10(2H),6.82(2H), 7.27(1H),7.37(2H),7.62 (1H),8.50(1H),8.60(1H) |
| 92 | 1 | —NMe₂ | 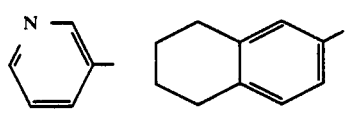 | | C₂₀H₂₁N₃S oil | 1.73(4H),2.68(4H), 3.10(6H),6.90(1H), 7.00-7.30(3H),7.53(1H) 8.37(1H),8.50(1H) |
| 93 | 1 | —NMe₂ | 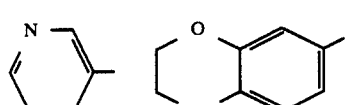 | | C₁₈H₁₇N₃O₂S oil | 3.13(6H),4.20(4H),6.70 (1H),6.90(1H),7.13(1H), 7.53(1H),8.40(1H), 8.50(1H) |
| 94 | 1 | —NMe₂ | 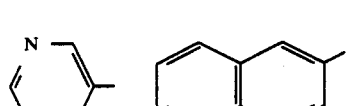 | | C₂₀H₁₇N₃S oil | 3.13(3H),7.06(1H),7.30-7.80(6H),8.03(1H),8.38 (1H),8.53(1H) |

| Cmpd No. | No. of W. Ex. based | R¹ | R² | R³ | Composition Formula m.p. |
|---|---|---|---|---|---|
| 95 | 1 | —NHEt | 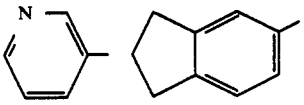 | | C₁₉H₁₉N₃S 172-173° |
| 96 | 1 | —NHMe | 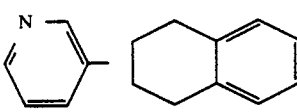 | | C₁₉H₁₉N₃S 158-159° |
| 97 | 1 | —NHEt | 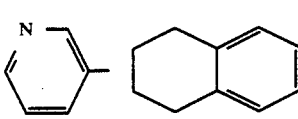 | | C₂₀H₂₁N₃S 164-165° |
| 98 | 1 | —NHEt | 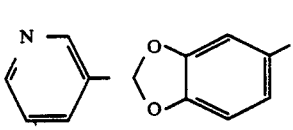 | | C₁₇H₁₅N₃O₂S 153-154° |
| 99 | 1 | —NHMe | 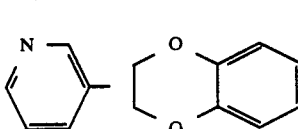 | | C₁₇H₁₅N₃O₂S 181-182° |
| 100 | 1 | —NHEt | 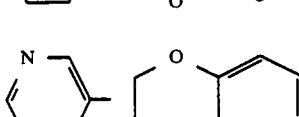 | | C₁₈H₁₇N₃O₂S 140-141° |

TABLE 1-continued

| 101 | 1 | —NHMe | [N-pyridyl-naphthyl structure] | C19H15N3S | 183–184° |

EXAMPLE 15

Examples of Pharmaceutical Composition

| (A) | Capsule | |
|---|---|---|
| | (1) Compound No. 1 | 50 mg |
| | (2) Cellulose fine powder | 45 mg |
| | (3) Lactose | 52 mg |
| | (4) Magnesium stearate | 13 mg |
| | Total | 160 mg |

All the materials were mixed and filled into a gelatin capsule.

| (B) | Soft Capsule | |
|---|---|---|
| | (1) Compound No. 7 | 20 mg |
| | (2) Corn starch oil | 130 mg |
| | Total | 150 mg |

A mixed solution of (1) and (2) were prepared and filled into a soft capsule by a conventional manner.

| (C) | Tablet | |
|---|---|---|
| | (1) Compound No. 48 | 50 mg |
| | (2) Lactose | 34 mg |
| | (3) Corn starch | 10.6 mg |
| | (4) Corn starch (gelatinized) | 5 mg |
| | (5) Magnesium stearate | 0.4 mg |
| | (6) Calcium Carboxymethyl cellulose | 20 mg |
| | Total | 120 mg |

All the materials were mixed and compressed by a tabletting machine to prepare a tablet in accordance with a conventional manner.

REFERENCE EXAMPLE 1

In 300 ml of anhydrous tetrahydrofuran was dissolved 33.2 ml of diisopropylamine, and the solution was cooled to −78° C., to which was added dropwise, while stirring, 148 ml of hexane solution of n-butyl lithium (1.6 M). The mixture was stirred for further 10 minutes at the same temperature, followed by dropwise addition of 20 g of β-picoline. The temperature was then raised up to −10°–0° C. and the mixture was stirred for 20 minutes, to which was added dropwise 19.4 g of ethyl p-anisole dissolved in 40 ml of anhydrous tetrahydrofuran. Then, the mixture was stirred for one hour at room temperature, followed by addition of about 100 ml of water. The organic solvent was evaporated off, and the concentrated solution was subjected to extraction with ethyl acetate. The extract solution was washed with water and dried on magnesium sulfate, followed by crystalliation from a mixture of ethyl acetate-isopropylether to give 20.8 g (yield: 85%) of 1-(4-methoxyphenyl)-2-(3-pyridyl)-ethanone, m.p. 71°–72° C.

By employing, instead of ethyl p-anisole, ethyl benzoate, ethyl 3,4-dimethoxybenzoate, ethyl 3,4,5-trimethoxybenzoate, ethyl 4-methoxymethoxy benzoate, methyl 4-fluorobenzoate, methyl 5-indanylcarboxylate, methyl 5,6,7,8-tetrahydro-2-naphthylcarboxylate, methyl 1,4-benzodioxan-6-carboxylate or methyl 2-naphthylcarboxylate, the process of the above Reference Example was conducted to give the following compounds, correspondingly:

1-phenyl-2-(3-pyridyl)ethanone, m.p. 44.5°–45.5° C.
1-(3,4-dimethoxyphenyl)-2-(3-pyridyl)ethanone m.p. 114°–115° C.
1-(3,4,5-trimethoxyphenyl)-2-(3-pyridyl)ethanone m.p. 104°–105° C.
1-(4-methoxymethoxyphenyl)-2-(3-pyridyl)ethanone m.p. 43°–44° C.
1-(4-fluorophenyl)-2-(3-pyridyl)ethanone, oily substance
1-(5-indanyl)-2-(3-pyridyl)ethanone m.p. 55°–56° C.
1-(5,6,7,8-tetrahydro-2-naphthyl)-2-(3-pyridyl)ethanone m.p. 65°–66° C.
1-(1,4-benzodioxan-6-yl)-2-(3-pyridyl)ethanol m.p. 89°–90° C.
1-(2-naphthyl)-2-(3-pyridyl)ethanone m.p. 69°–70° C.

Likewise, instead of β-picoline, use of α-picoline, γ-picoline or 3.5-lutidine gives the following compounds, correspondingly:

1-phenyl-2-(2-pyridyl)ethanone, m.p. 59°–60° C.
1-(4-methoxyphenyl)-2-(2-pyridyl)ethanone, m.p. 77°–78° C.
1-phenyl-2-(4-pyridyl)ethanone, m.p. 109°–110° C.
1-(4-methoxyphenyl)-2-(4-pyridyl)ethanone, m.p. 103°–104° C.
1-phenyl-2-(5-methyl-3-pyridyl)ethanone, m.p. 53°54° C.
1-(4-ethylphenyl)-2-(3-pyridyl)ethanone, m.p. 80°–81° C.
1-(3,4-methylenedioxyphenyl)-2-(3-pyridyl)ethanone, m.p. 98°–99° C.

REFERENCE EXAMPLE 2

In 36 ml of acetic acid was dissolved 6.85 g of 1-(4-methoxyphenyl)-2-(3-pyridyl)ethanone obtained by Reference Example 1. To the solution was added 1.7 ml of bromine, and the mixture was stirred at 80° C. for 3 hours. The reaction solution was cooled with ice-water, and the resulting crystals were collected by filtration. The crystals were washed with ethanol and ethylether, successively, followed by drying to give 10.4 g (yield 89%) of hydrobromide of 2-bromo-1-(4-methoxyphenyl)-2-(3-pyridyl)ethanone, m.p. 188°–195° C. By a similar method to Reference Example 2, hydrobromides of the following compounds were obtained.

2-bromo-1-phenyl-2-(3-pyridyl)ethanone, m.p.[*1] 208°–215° C.
2-bromo-1-(3,4-dimethoxyphenyl)-2-(3-pyridyl)ethanone, m.p.[*1] 191°–193° C.
2-bromo-1-(3,4,5-trimethoxyphenyl)-2-(3-pyridyl)ethanone, m.p.[*1] 184°–186° C.
2-bromo-1-(4-hydroxyphenyl)-2-(3-pyridyl)ethanone[*2]
2-bromo-1-(4-fluorophenyl)-2-(3-pyridyl)ethanone, m.p.[*1] 189°–191° C.

2-bromo-1-phenyl-2-(2-pyridyl)ethanone, m.p.*¹ 180°-181° C.
2-bromo-1-(4-methoxyphenyl)-2-(2-pyridyl)ethanone, m.p.*¹ 170°-171° C.
2-bromo-1-phenyl-2-(4-pyridyl)ethane, m.p.*¹ 230°-232° C.
2-bromo-1-(4-methoxyphenyl)-2-(4-pyridyl)ethanone, m.p.*¹ 207°-209° C.
2-bromo-1-pheny-2-(5-methyl-3-pyridyl)ethanone, m.p.*¹ 189°-193° C.
2-bromo-1-(4-ethylphenyl)-2-(3-pyridyl)ethanone, m.p.*¹ 145°-146° C.
2-bromo-1-(3,4-methylenedioxyphenyl)-2-(3-pyridyl)ethanone, m.p.*¹ 174°-175° C.
2-bromo-1-(5-indanyl)-2-(3-pyridyl)ethanone m.p.*¹ 177°-178° C.
2-bromo-1-(5,6,7,8-tetrahydro-2-naphthyl)-2-(3-pyridyl)ethanone m.p.*¹ 160°-162° C.
2-bromo-1-(1,4-benzodioxane-6-yl)-2-(3-pyridyl)*ethanone ²
2-bromo-1-(2-naphthyl)-2-(3-pyridyl)ethanone m.p.*¹ 197°-199° C.

The melting point bearing *1 is that of hydrobromide. The hydrobromide bearing *2 was directly used for thiazole-forming reaction without purification.

REFERENCE EXAMPLE 3

In 80 ml of anhydrous tetrahydrofuran was dissolved 8.86 ml of diisopropylamine. The solution was cooled to −10°, to which was added dropwise 39.5 ml of a hexanoic solution of n-butyl lithium (1.6M). Then, the mixture was stirred for 30 minutes at the same temperature, followed by dropwise addition of 5.34 g of β-picoline. The mixture was stirred for 30 minutes, to which was added dropwise 5 g of 5-methoxycarbonyl indane dissolved in 10 ml of anhydrous tetrohydrofuran. Then, the mixture was stirred for one hour at room temperature, followed by addition of about 25 ml of water. The organic solvent was exaporated off under reduced pressure. The concentrated solution was subjected to extraction with ethylacetate. The extract solution was washed with water, dried on magnesium sulfate and concentrated. The concentrate was crystallized from ethylacetate-isopropylether to give 5.6 g (yield 82%) of 1-(5-indanyl)-2-(3-pyridyl)-ethanone, m.p. 55°-56° C.

REFERENCE EXAMPLE 4

In 20 ml of acetic acid was dissolved 4.3 g of 1-(5-indanyl)-2-(3-pyridyl)ethanone. To the solution was added 0.93 ml of bromine, which was stirred for one hour at 80°, then the reaction solution was cooled. Addition of 80 ml of ethylether gives a layer of oily substance. The supernatant was discorded, and the remainder was dissolved in 50 ml of acetonitrile. The solution was cooled to give 6.2 g of 2-bromo-1-(5-indanyl)-2-(3-pyridyl)ethanone hydrobromide, m.p. 176°-177° C. The yield was 86%.

REFERENCE EXAMPLE 5

In 6 ml of thionyl chloride was suspended 5.0 g of piperonylic acid. The suspension was refluxed for 8 hours. Excess volume of thionyl chloride was evaporated off under reduced pressure to give crude crystals of piperonylic acid chloride.

The crystals were dissolved in 10 ml of methylene chloride. The solution was slowly added dropwise, while stirring at 0°, to a solution of 1.7 g of propylene imine and 3.3 g of petroreum ether in 10 ml of methylene chloride. Then, the mixture was further stirred for 30 minutes. The solvent was evaporated off under reduced pressure. To the residue was added water, which was subjected to extraction with ethyl acetate. The extract solution was washed with water, dried and concentrated under reduced pressure. Thus-obtained crude product was purified by means of a silica-gel chromatography (eluent: ethyl acetate) to give 4.37 g (yield 69%) of N-piperonyloyl propylene imine.

REFERENCE EXAMPLE 6

A lithium diisopropyl amide solution was prepared at 0° from 3.2 ml of diisopropylamine, 14.5 ml of n-butyl lithium hexane solution (1.6 M) and 60 ml of tetrahydrofuran. To thus-prepared solution was added 1.95 g of β-picoline, 2nd the mixture was stirred for 30 minutes at 0°. To the mixture was added slowly dropwise a tetrahydrofuran solution of 4.3 g of N-piperonyl propylene imine, then the whole mixture was stirred for one hour. To the reaction solution was added N-hydrochloric acid until pH of the solution becomes acid side. The organic solvent was evaporated off under reduced pressure. The aqueous layer was made weakly alkaline by the use of an aqueous solution of sodium bicarbonate, followed by extraction with ethyl acetate. The extract solution was washed with water, dried and concentrated under reduced pressure. The residue was purified by means of a silica-gel column chromatography (eluent: ethyl acetate), followed by recrystallization from ethyl acetate-isopropyl ether to give 3.2 g (yield : 63%) of 1-piperonyl-2-(3-pyridyl)-ethanone, m.p. 98°-99° C.

EXPERIMENTAL EXAMPLE

A. Anti-inflammatory activity; Carrageenin edema (C.E. Method)

The anti-inflammatory activities of test compounds were estimated in a group [Six Jcl: SD rats (male, weighing 180-220 g)] by the method of Winter et al. [Proc. Soc. Exp. Biol. 111, 544 (1962)].

After measuring the volume of the right-hind paw (a), the rats were given orally 5 ml of water. One hour after oral administration of the test compounds, 0.05 ml each of a 1% carrageenin solution in physiological saline was subcutaneously injected at the sole of right-hind paw. Three hr. later, the volume of the right-hind paw was measured (b). The volume of edema was obtained from the difference (a−b) between the two volumes. By comparing the volume of edema of the group, to which test compound was administered, with that of the group, to which no test compound was administered, an inhibitory effect of the compound on the edema was determined.

B. Analgesic action: Phenylquinone writhing syndrome (P.Q. Method)

The test was conducted by following the method Siegmund et al. [Proc. Soc. exp. Biol. Med. 95, 729 (1957).] employing a group [ten Slc:ICR mice (male, 4-weeks old, weighing 20±2 g)]. Test compounds were administered orally 30 minutes before intraperitoneal injection of 0.02% phenylquinone by 0.1 ml/body weight of 10 g. Then, the frequency of responses, i.e. writhing and stretching was counted in each animal for 20 minutes. The average frequencies in the test group and the control group were compared, and an inhibitory effect of the compounds on this response was determined.

C. Water-immersion stress-induced gastric ulcer (W.I. Method)

Male SD rats (7-weeks old, weighing 190–240 g) were used after a 24 hr. fast in groups of six animals. According to the method of Takagi and Okabe [Jpn. J. Pharmacol., 18, 9 (1968)], the animals were placed in a stress cage made of stainless steel and immersed vertically to the level of xiphoid process in a water bath maintained at 23° C. for five hours. The length (mm) of individual lesions in fundic mucosa was measured under a dissecting microscope with a 1-mm square-grid eye piece (X10), and the sum of the length of individual lesions for each stomach was used as an ulcer index. The ulcer index of the test group was compared with that of the control group, and the inhibition ratio was calculated.

D. Acute toxicity Test in mice

Five-weeks old ICR-male mice were used in groups of five animals. Each animal was orally administered with 500 mg/kg of each test compound. Then, during the subsequent one week, the number of dead animals was counted. Representable examples of the results of the foregoing tests were shown in Table 2.

TABLE 2

| Cmpd No | C.E. Method | P.Q. Method 50 mg/kg | W.I. Method 50 mg/kg | Acute Toxicity |
|---|---|---|---|---|
| 1 | 60 | 96.8 (25 mg/kg) | 86 | 0/5 |
| 2 | 77.1 | 52.6 | 70 | 0/5 |
| 4 | 63.7 | 78.9 | 74 | 0/5 |
| 9 | 16.9 | 40.5 | 71 | 0/5 |
| 13 | 7.0 | 67.5 | 66 | 0/5 |
| 17 | 48.2 | 80.7 | 79 | 0/5 |
| 28 | 15.7 | 63.3 | 33 | 0/5 |

What is claimed is:

1. A compound of the formula:

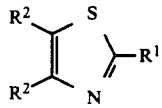

wherein $R^1$ is (1) an alkyl group having 1 to 10 carbon atoms, which is unsubstituted or substituted by hydroxyl, amino, a lower alkylamino having 1 to 4 carbon atoms, carboxyl or a lower alkoxycarbonyl having 2 to 5 carbon atoms, (2) an alkenyl group having 2 to 4 carbon atoms, which is unsubstituted or substituted by hydroxyl, carboxyl or a lower alkylamino group having 1 to 4 carbon atoms, (3) a phenyl or naphthyl group which is unsubstituted or substituted by 1 to 3 substituents selected from the group consisting of carboxyl, halogen, 2-carboxy-ethenyl, 2-carboxy-1-propenyl, acetoxy and lower alkyl having 1 to 4 carbon atoms, (4) an aralkyl group having 7 to 12 carbon atoms, which is unsubstituted or substituted by methoxy or halogen, (5) cycloalkyl having 3 to 7 carbon atoms, which is unsubstituted or substituted by alkyl having 1 to 3 carbon atoms, (6) an amino group which is unsubstituted or substituted by one or two substituents selected from the group consisting of lower alkyl having 1 to 4 carbon atoms, aralkyl having 7 to 10 carbon atoms, phenyl, pyridyl, 5-methyl-3-pyridyl, 4-methyl-2-pyridyl, $C^{1-4}$-alkyl-O-CO-CH$_2$-CO-, lower alkylcarbonyl having 2 to 5 carbon atoms, carboxycarbonyl, lower alkoxycarbonylcarbonyl having 3 to 6 carbon atoms, lower alkoxycarbonyl having 2 to 4 carbon atoms, and halogenoalkoxycarbonyl having 2 to 5 carbon atoms, or (7) a piperidino or pyrrolidino group;

$R_2$ is a pyridyl group which is unsubstituted or substituted by alkyl group having 1 to 4 carbon atoms, and $R^3$ is a phenyl or naphthyl group which is unsubstituted or substituted by 1 to 3 substituents selected from the group consisting of lower alkoxy having 1 to 4 carbon atoms, lower alkyl having 1 to 4 carbon atoms, hydroxyl, halogen, trimethylene and methylenedioxy, or a pharmaceutically acceptable salt thereof.

2. A compound as claimed in claim 1, wherein the salt is a pharmacologically acceptable salt.

3. A compound as claimed in claim 1, wherein $R^2$ is 3-pyridyl group which is unsubstituted or substituted with methyl.

4. A compound as claimed in claim 1, wherein the compound is 4-(4-methoxyphenyl)-2-methylamino-5-(3-pyridyl)-1,3-thiazole.

5. A compound as claimed in claim 1, wherein the compound is 4-(4-fluorophenyl)2-methylamino-5-(3-pyridyl)-1,3-thiazole.

6. A compound as claimed in claim 1, wherein the compound is 4-(3,4-methylenedioxyphenyl)-2-methylamino-5-(3-pyridyl)-1,3-thiazole.

7. An analgesic, anti-pyretic, anti-inflammatory and anti-ulcer pharmaceutical composition, which comprises as an active ingredient, an effective amount of a compound of the formula:

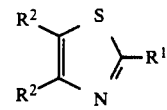

wherein $R^1$ is (1) an alkyl group having 1 to 10 carbon atoms, which is unsubstituted or substituted by hydroxyl, amino, a lower alkylamino having 1 to 4 carbon atoms, carboxyl or a lower alkoxycarbonyl having 2 to 5 carbon atoms, (2) an alkenyl group having 2 to 4 carbon atoms, which is unsubstituted or substituted by hydroxyl, carboxyl or a lower alkylamino group having 1 to 4 carbon atoms, (3) a phenyl or naphthyl group which is unsubstituted or substituted by 1 to 3 substituents selected from the group consisting of carboxyl, halogen, 2-carboxy-ethenyl, 2-carboxyl-1-propenyl, acetoxy and lower alkyl having 1 to 4 carbon atoms, (4) an aralkyl group having 7 to 12 carbon atoms, which is unsubstituted or substituted by methoxy or halogen, (5) cycloalkyl having 3 to 7 carbon atoms, which is unsubstituted or substituted by alkyl having 1 to 3 carbon atoms, (6) an amino group which is unsubstituted or substituted by one or two substituents selected from the group consisting of lower alkyl having 1 to 4 carbon atoms, aralkyl having 7 to 10 carbon atoms, phenyl, pyridyl, 5-methyl-3-pyridyl, 4-methyl-2-pyridyl, $C^{1-4}$-alkyl-O-CO-CH$_2$-CO-, lower alkylcarbonyl having 2 to 5 carbon atoms, carboxycarbonyl, lower alkoxycarbonylcarbonyl having 3 to 6 carbon atoms, lower alkoxycarbonyl having 2 to 4 carbon atoms, and halogenoalkoxycarbonyl having 2 to 5 carbon atoms, or (7) a piperidino or pyrrolidino group;

$R_2$ is a pyridyl group which is unsubstituted or substituted by an alkyl group having 1 to 4 carbon atoms, and $R^3$ is a phenyl or naphthyl group which is unsubstituted or substituted by 1 to 3 substituents selected from the group consisting of lower alkoxy having 1 to 4 carbon atoms, lower alkyl having 1 to 4 carbon atoms, hydroxyl, halogen, trimethylene and methylenedioxy, or a pharmaceutically acceptable salt thereof and a pharmacuetically acceptable carrier therefor.

* * * * *